United States Patent [19]

Pennig

[11] Patent Number: 5,484,438
[45] Date of Patent: Jan. 16, 1996

[54] INTRAMEDULLARY NAIL WITH SCREW-RECEIVING SOLID INSERT

[76] Inventor: Dietmar Pennig, Hans-Driesch-Strasse 12, 50935 Köln, Germany

[21] Appl. No.: 344,223

[22] Filed: Nov. 23, 1994

Related U.S. Application Data

[63] Continuation of Ser. No. 101,838, filed as PCT/DE93/00135, Feb. 11, 1193, abandoned.

[30] Foreign Application Priority Data

Feb. 13, 1992 [DE] Germany .................. 42 04 246.1
Feb. 20, 1992 [DE] Germany .................. 42 05 118.5

[51] Int. Cl.[6] .................................................. A61B 17/72
[52] U.S. Cl. ............................ 606/64; 606/62; 606/76
[58] Field of Search ........................... 606/64, 62, 63, 606/67, 68, 65, 66, 75, 77, 76, 95, 104

[56] References Cited

U.S. PATENT DOCUMENTS

| | | | |
|---|---|---|---|
| 3,596,656 | 8/1971 | Kaute | 606/67 |
| 4,338,926 | 7/1982 | Kummer et al. | 606/62 |
| 4,457,301 | 7/1984 | Walker | 606/62 |
| 4,733,654 | 3/1988 | Marino | 606/64 |
| 4,851,008 | 7/1989 | Johnson | 623/16 |
| 4,919,666 | 4/1990 | Buchhorn et al. | 623/16 |
| 5,127,913 | 7/1992 | Thomas, Jr. | 606/62 |

FOREIGN PATENT DOCUMENTS 1692566  11/1991  U.S.S.R. .................. 606/62

Primary Examiner—Stephen C. Pellegrino
Assistant Examiner—Guy Tucker
Attorney, Agent, or Firm—Hopgood, Calimafde, Kalil & Judlowe

[57] ABSTRACT

A medullary nail has a plug-like insert arranged in the end region of the nail. The insert consists of a readily drillable or screwable material that is suitable for receiving a corresponding attachment element such as a bone screw or a bone pin. The medullary nail is otherwise of standard metal construction, preferably of stainless steel.

9 Claims, 1 Drawing Sheet

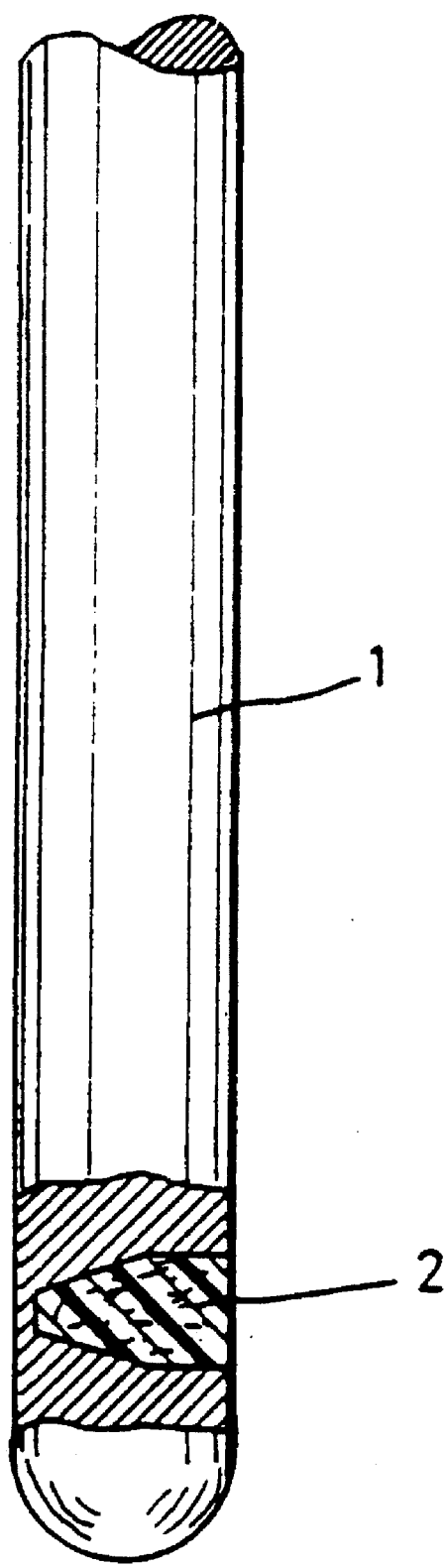

INTRAMEDULLARY NAIL WITH SCREW-RECEIVING SOLID INSERT

This is a continuation of U.S. patent application Ser. No. 08/101,838, filed Aug. 4, 1993, as PCT/DE93/00135, Feb. 11, 1993.

BACKGROUND OF THE INVENTION

The present invention relates to an intramedullary nail construction.

In orthopedic practice today, it is no problem for lower-arm and femur nails to be securely retained in their associated bone sections, using bone-anchoring screws which extend transverse to the longitudinal axis of the nail. But, in the case of a humerus nail (German Application DE 88 11 634 U1), there is the danger that by drilling the required holes for the bone-anchoring screws, nerves may be injured. Therefore, to date, it has not been possible to securely fix the implanted position of a humerus nail.

BRIEF STATEMENT OF THE INVENTION

It is the object of the present invention to provide a medullary nail with which it is possible to dispense with drilling through the cortex on both sides of the nail, i.e., the nail is fixed in position only on one side by an attachment pin or a corresponding screw driven into the cortex and into the medullary nail.

The invention achieves this object by providing a metal medullary nail with a plug-like insert in the distal-end region of the nail. The insert extends transverse to the longitudinal axis of the nail, and is exposed at the outer surface of the nail, at least on one side of the nail. And the insert consists of a material which can readily be drilled, or into which a screw can readily be driven.

By this measure, it is now possible to drill through the cortex of the humerus only on one side and to introduce through this drilled hole a screw or a pin which at its outer end is held securely in the cortex and which at its inner end is secured into the insert within the nail, without having the screw or pin protrude at the other side or out of the medullary nail. In this way, an injury or damage to the sensitive nerves on the other side of the bone is reliably excluded.

It is a feature of the invention that the insert be arranged in one or more longitudinally or otherwise spaced blind holes or in cylindrical holes which are cylindrical over a major fraction of their length but then taper conically so that, in manufacturing a medullary nail of the invention, the process of filling the hole with insert material can be free of voids or cavities created by inclusions of air, or the like.

The insert may suitably be of plastic material, and it can also advantageously be made of a material which is biodegradable, wherein the period for such biological degradation is, of course, greater than is required for healing a fracture of the humerus, thereby enabling nail removal in due time. By using biodegradable material, one can be assured that splinters which result from drilling the insert cannot lead to inflammations or the like.

BRIEF DESCRIPTION OF THE DRAWINGS

A preferred embodiment of the invention will be described in detail, with reference to the accompanying drawing which is a view in side elevation of the distal portion of a medullary nail, the same being broken-away and in longitudinal section near the distal end of the nail.

DESCRIPTION OF THE PREFERRED EMBODIMENT

In the drawing, an end region of a medullary nail 1 is seen to have been provided with a solid insert 2 which, in the embodiment shown, is contained in a generally cylindrical hole, developed as blind hole, on an axis transverse to and intersecting the axis of nail 1. The insert 2 preferably consists of a biodegradable material. After drilling through from one side only of a bone having a medullary nail already in place, a screw can now be driven into the insert, thereby fixedly positioning the end region of the nail, and resulting in a positional fix of the nail to the cortex.

What is claimed is:

1. A medullary nail of metal comprising a cylindrical body having a longitudinal axis and a local cavity near the end region of the nail, said cavity extending transverse to the longitudinal axis to a depth exceeding the radius of the nail and open at least on one side of the nail, and a plug-like insert of a single material solidly filling the cavity and externally conforming to and continuous with the local outer surface profile of the nail and consisting of a material which can be readily drilled or into which a screw can readily be driven.

2. A medullary nail according to claim 1, wherein the local cavity is a blind hole in the nail.

3. A medullary nail according to claim 1, wherein the local cavity is a cylindrical hole transverse to the longitudinal axis of the nail, said hole tapering conically toward the other side of the nail.

4. A medullary nail according to claim 1, in which said insert is one of a plurality of inserts, in longitudinally spaced relation along the nail.

5. A medullary nail according to claim 1, wherein the insert consists of a plastic material.

6. A medullary nail according to claim 7, wherein the plastic of said insert is biodegradable.

7. As an article of manufacture, a medullary nail comprising an elongate cylindrical metal body having a transversely oriented cavity which extends to a depth exceeding the radius of the nail in a direction generally diametrically of the nail from one side of the nail but terminates short of the other side of the nail, and a single non-metallic screw-anchoring material solidly filling said cavity and conforming to the outer surface of the nail.

8. The method of fixing a medullary nail in a bone in which the nail has been inserted in the medullary canal of the bone, wherein the nail has a longitudinal axis and a local cavity near the distal-end region of the nail, said cavity extending transverse to the longitudinal axis and open at least on one side of the nail, there being a solid filling of the cavity with a material which can be readily drilled or into which a screw can readily be driven, said method comprising the step of selecting the nail for the provision of biodegradable material in the filling, and the subsequent step of driving a fixation screw into the filling via a single alignment through a portion of bone cortex adjacent to the filling.

9. The method of fixing a medullary nail in a bone in which the nail has been inserted in the medullary canal of the bone, wherein the nail has a longitudinal axis and a local cavity near the distal-end region of the nail, said cavity extending transverse to the longitudinal axis and open at least on one side of the nail, there being a solid filling of the cavity with a material which can be readily drilled or into which a screw can readily be driven, said method comprising the step of drilling through cortical tissue of the bone and into said filling on a single alignment with a portion of the filling, and then driving a fixation screw through the drilled hole in the cortex and the filling.

* * * * *